(12) United States Patent
Niemi et al.

(10) Patent No.: US 6,342,205 B1
(45) Date of Patent: Jan. 29, 2002

(54) HIGH WATER CONTENT DENTIFRICE COMPOSITION AND METHOD OF MAKING THE SAME

(75) Inventors: Taina H. Niemi; L. Bjarne Martensson, both of Hamina (FI)

(73) Assignee: J. M. Huber Corporation, Edison, NJ (US)

(*) Notice: Subject to any disclaimer, the term of this patent is extended or adjusted under 35 U.S.C. 154(b) by 0 days.

(21) Appl. No.: 09/430,136

(22) Filed: Oct. 29, 1999

(51) Int. Cl.[7] ................................................ A61K 7/16
(52) U.S. Cl. ......................................................... 424/49
(58) Field of Search ..................... 424/49–58

(56) References Cited

U.S. PATENT DOCUMENTS

| | | | |
|---|---|---|---|
| 4,140,757 A | * 2/1979 | Wason et al. | 424/49 |
| 4,264,579 A | * 4/1981 | Carr | 424/49 |
| 4,435,380 A | * 3/1984 | Pader | 424/49 |
| 4,599,363 A | * 7/1986 | Miles et al. | 424/49 |
| 4,618,488 A | 10/1986 | Maeyama | 424/49 |
| 4,701,319 A | * 10/1987 | Woo | 424/49 |
| 5,275,803 A | * 1/1994 | Dawson | 424/49 |
| 5,310,543 A | * 5/1994 | Dawson | 424/49 |
| 5,695,746 A | * 12/1997 | Garlick et al. | 424/49 |
| 6,159,446 A | * 12/2000 | Randive et al. | 424/49 |

FOREIGN PATENT DOCUMENTS

| | | | | |
|---|---|---|---|---|
| WO | WO 95/22958 | | 8/1995 | A61K/7/16 |
| WO | 96/06593 | * | 3/1996 | |

* cited by examiner

*Primary Examiner*—Shep K. Rose
(74) *Attorney, Agent, or Firm*—Carlos Nieves

(57) ABSTRACT

A high water content dentifrice composition having a viscosity greater than about 200,000 centipoise (cP) comprising a water content greater than about 50% by weight, abrasive material, binder, and a polyol humectant. This invention provides a high water content dentifrice composition that has acceptable stability, mouthfeel and rheological properties. The inventive dentifrice composition also is relatively inexpensive to manufacture.

13 Claims, No Drawings

HIGH WATER CONTENT DENTIFRICE COMPOSITION AND METHOD OF MAKING THE SAME

TECHNICAL FIELD

This invention relates to a high water content dentifrice composition and, more particularly, to such a dentifrice composition that has a water content of greater than 50% by weight and a viscosity of greater than 200,000 centipoise (cP). The invention also relates to a method of making such a dentifrice composition.

BACKGROUND OF THE INVENTION

Dentifrice compositions generally contain combinations of an abrasive material with one or typically several of a thickener system, a humectant system, a flavoring agent and a foaming agent. Other ingredients commonly found in dentifrice compositions such as toothpaste formulations include detergents or surfactants, coloring or whitening agents, preservatives, antibacterial agents and fluorides.

The use of silica as the abrasive component in toothpaste formulations dramatically changed dentifrice technology over twenty years ago when fluoride became established as an anticaries active ingredient for prevention of tooth decay. Unlike calcium carbonate, dental-grade silica proved to be compatible with most fluoride sources. Its predominant use in dentifrice in industrialized countries has contributed to a major decline in caries and tooth decay among school-aged children. The World Health Organization has as a top priority elimination of dental caries. The Oral Health Division of Noncommunicable Diseases, World Health Organization, published in 1998 a report entitled "School-based Primary Preventive Programme for Children". One objective of the project described in this report is to encourage companies to produce "an affordable fluoride containing toothpaste."

While the beneficial impact of the use of a fluoride-containing dentifrice on oral hygiene and dental health is well documented, such compositions are relatively expensive for many consumers and, therefore are not widely affordable in many developing countries. The cost of a given dentifrice formulation is often dictated by the amount of water that can be incorporated therein. Given the economics involved, the dentifrice formulation ideally would contain as high a water fraction as possible without sacrificing the needed performance and aesthetics. Nonetheless, the notion of significantly increasing the water content per se of a dentifrice raises concerns of undermining, for example, the stability and uniformity of the dentifrice formulation, its ability to retain its body and shape without experiencing inordinate sagging when extruded upon toothbrush bristles in order to sufficiently sit on the bristles, or the tendency of the formulation not to readily seep out of the dispenser tube when opened. In practice, merely increasing the water content in conventional dentifrice formulations, all other things kept equal, has been observed to have a deleterious impact on stability, mouthfeel and rheological properties.

In any event, liquid dentifrice compositions have been marketed, particularly but not exclusively in Europe, for many years. These compositions could contain relatively high amounts of water, but they have lower viscosity and thinner mouthfeel than typical toothpaste formulations to which many other consumers have grown accustomed and prefer from aesthetical and performance standpoints. Many consumers will not accept a runny toothpaste. On the other hand, although a toothpaste needs body, it cannot be lumpy or overly sticky either. Examples of measured viscosity values for several sampled commercial liquid dentifrice compositions are provided in Table A below.

TABLE A

| Description | Manufacturer | Viscosity,cP |
| --- | --- | --- |
| ODOL-MBD gel | Linger & Fischer, Germany | 21,000 |
| FISCO-DENT gel | Maxim, Germany | 53,000 |
| VADEMECUM | Henkel, Sweden | 14,500 |
| THERA-MED | Schwartzkopf & Henkel, Germany | 25,500 |
| PEARL DROPS opaque | Carter-Wallace, UK | 106,000 |

In view of the above, it can be appreciated that a challenge and need has existed in the dentifrice field for development of a liquid dentifrice that can sustain increased water content yet without sacrificing the desired performance and aesthetics.

SUMMARY OF THE INVENTION

The present invention overcomes the deficiencies of the prior art and meets the challenges discussed above. This invention provides a high water content dentifrice composition that has acceptable stability, mouthfeel and Theological properties. The inventive dentifrice composition also is relatively inexpensive to manufacture, which can translate into a more affordable product for consumers. To achieve these and other advantages, benefits, and enhancements, a high water content dentifrice composition having a viscosity greater than about 200,000 centipoise (cP) is provided according to this invention comprising a water content greater than about 50% by weight, abrasive material, binder, and polyol humectant.

In accordance with one embodiment of the present invention, the high water content dentifrice composition having a viscosity greater than 200,000 cP and including water in an amount of greater than about 50% by weight is formulated as an admixture therewith of abrasive material in an amount of about 8% to about 18% by weight, silica thickener in an amount of about 8% to about 15% by weight, binder in an amount of about 0.5% to about 1.5% by weight, and polyol humectant in an amount of about 1% to about 20% by weight.

In order to render the inventive dentifrice compositions "therapeutic" in nature, the dentifrice compositions of the present invention typically also will contain a water soluble fluorine-containing compound and/or other active compound(s) insofar as having a beneficial effect on the care and hygiene of the oral cavity by protecting the teeth against decay, reducing the acid solubility of the tooth enamel, reducing plaque, and/or reducing oral bacteria, among other things. For instance, fluorine-containing compounds providing one or more of these properties can be included in an effective, non-toxic amount in the formulation, which generally can range from about 0.01 to about 1% by weight of the overall formulation.

Other objects, features and advantages will be readily apparent from the following detailed description of preferred embodiments thereof.

DETAILED DESCRIPTION OF THE PREFERRED EMBODIMENTS

In accordance with the preceding summary, the present invention is directed toward a high water content dentifrice composition that has acceptable rheology, mouthfeel and stability. Generally, the inventive dentifrice composition will include water in an amount of greater than about 50%, abrasive material in an amount of about 8% to about 18%, silica thickener in an amount of about 8% to about 15%, binder in an amount of about 0.5% to about 1.5%, and a polyol humectant in an amount of about 1% to about 20% by weight. All the percentages by weight described and mentioned in this application for the respective components of the inventive dentifrice composition are based on the total (overall) weight of all the combined ingredients of the dentifrice composition product.

The term "dentifrice" as used herein, includes therapeutic opaque paste formulations. In order to be "therapeutic", the dentifrice compositions of the present invention typically will also contain a water soluble fluorine-containing compound and/or other active compound(s) insofar as having a beneficial effect on the care and hygiene of the oral cavity by protecting the teeth against decay (i.e., anti-caries agents), reducing the acid solubility of the tooth enamel, reducing plaque, and/or reducing oral bacteria, among other things. Fluorine-containing compounds providing one or more of these properties are included in an effective, non-toxic amount in the formulation, which generally ranges from about 0.01 to about 1% by weight of the overall formulation. The term "therapeutic" as used herein to characterize the dentifrice composition, includes therapeutic agents such as sodium fluoride, stannous fluoride, sodium monofluorophosphate, potassium fluoride, potassium stannous fluoride, triclosan, chlorhexidine, sodium fluorostannate, stannous chlorofluoride, amine fluoride, singly or in combinations thereof, and other comparable anti-decay and/or anti-bacterial agents commonly used in dentifrice compositions which release or dissociate fluorine-containing ions in water. The total water content of the present invention is greater than about 50% by weight, preferably ranges from about 50% by weight to about 85% by weight, and more preferably ranges from about 60% to about 70% by weight of the overall dentifrice composition. The percentage (%) by weight of water described herein means the total or combined weight of water present in the composition water including not only straight water additions but also other sources of water contributed from additives and adjuvants that admix with the overall formulation, such as, for example, water present in a humectant formulation such as sorbitol. The high water content results in the ability to manufacture a relatively low cost dentifrice that can be sold and marketed in developing countries throughout the world.

The abrasive material is preferably an amorphous precipitated silica such as Zeodent® 113 silica. Other preferred amorphous precipitated silica abrasives include Zeodent® 115, Zeodent® 623 and Zeodent® 124 silicas. Zeodent® silicas are available from J. M. Huber Corporation of Edison, N.J. Typical properties of these silicas are listed in Table B below.

For purposes of this application, the properties reported in Table B are determined as follows. Oil absorption, using linseed oil, is determined by the rubout method. This method is based on a principle of mixing oil with a silica by rubbing with a spatula on a smooth surface until a stiff putty-like paste is formed. By measuring the quantity of oil required to have a paste mixture which will curl when spread out, one can calculate the oil absorption value of the silica—the value which represents the volume of oil required per unit weight of silica to saturate the silica sorptive capacity. Calculation of the oil absorption value was done as follows:

$$\text{Oil absorption} = \frac{\text{cm}^3 \text{ oil absorbed}}{\text{weight of silica, grams}} \times 100$$

$$= \text{cm}^3 \text{ oil}/100 \text{ gram silica}$$

Particle size is determined using a Leeds and Northrup Microtrac II. A laser beam is projected through a transparent cell which contains a stream of moving particles suspended in a liquid. Light rays which strike the particles are scattered through angles which are inversely proportional to their sizes. The photodetector array measures the quantity of light at several predetermined angles. Electrical signals proportional to the measured light flux values are then processed by a microcomputer system to form a multi-channel histogram of the particle size distribution.

Surface area is determined by the BET nitrogen adsorption methods of Brunaur et al., *J. Am. Chem. Soc.*, 60, 309 (1938).

Pore volume (mercury pore volume) is determined using an Autopore II 9220 Porosimeter (Micromeritics Corporation). This instrument measures the void volume and pore size distribution of various materials. Mercury is forced into the voids as a function of pressure and the volume of mercury intruded per gram of sample is calculated at each pressure setting. Total pore volume expressed herein represent the cumulative volume of mercury intruded at pressures from vacuum to 60,000 psi. Increments in volume (cc/g) at each pressure setting are plotted against the pore radius corresponding to the pressure setting increments. The peak in the intruded volume versus pore radius curve corresponds to the mode in the pore size distribution and identifies the most common pore size in the sample.

Pour density is determined by weighing 100.0 grams product into a 250-ml graduated cylinder and recording the volume occupied.

Pack or tapped density is determined by weighing 100.0 grams of product into a 250-mL plastic graduated cylinder with a flat bottom. The cylinder is closed with a rubber stopper, placed on the tap density machine and run for 15 minutes. The tap density machine is a conventional motor-gear reducer drive operating a cam at 60 rpm. The cam is cut or designed to raise and drop the cylinder a distance of 2.25 in. (5.715 cm) every second. The cylinder is held in position

TABLE B

|  | Oil Abs. cm$^3$/100 g | APS $\mu$m | BET m$^2$/g | Pore Vol. cm$^3$/g | Pour density g/cm$^3$ | Pack Density g/cm$^3$ | Silica RDA |
|---|---|---|---|---|---|---|---|
| Zeodent 113 | 91 | 9 | 84 | 2.0 | 0.26 | 0.41 | 90 |
| Zeodent 115 | 98 | 10 | 85 | 2.6 | 0.21 | 0.43 | 80 |
| Zeodent 124 | 70 | 9 | 70 | 2 | 0.28 | 0.38 | 135 |
| Zeodent 623 | 105 | 9 | 250 | 2 | 0.26 | 0.40 | 75 | by guide brackets. Record the volume occupied by the product after tapping and calculate pack density in g/ml.

It should be noted that not only amorphous precipitated silicas but also other fluoride compatible abrasive materials could be utilized such as silica gel, alumina, aluminosilicate, dicalcium phosphate, chalk and precipitated calcium carbonate, used singly or in combinations thereof. The purpose of the abrasive material in the dentifrice formulation is to remove stains on the teeth, which cannot typically be removed by toothbrush bristles. The abrasive material also provides for general cleaning and plaque removal.

In addition to being fluoride compatible, the abrasive material should have a RDA value of from about 30 to about 150. In dentifrice formulations for children, the abrasive material preferably has a RDA value of from about 30 to about 50. In dentifrice formulations for adults, the abrasive material preferably has an RDA value of from about 50 to about 90. RDA stands for Radioactive Dentin Abrasion Test. The procedure for determining RDA follows the method recommended by the American Dental Association (Journal of Dental Research 55 (4) 563, 1976). In the recommended procedure, human teeth are irradiated with a neutron flux and subjected to a standard brushing regime. The radioactive phosphorous 32 removed from the dentin in the roots is used as the index of the abrasion of the dentifrice tested. A reference slurry containing 10 g of calcium pyrophosphate in 50 ml of 0.5% aqueous solution of sodium carboxymethyl cellulose is also measured and the RDA of this mixture is arbitrarily taken as 100.

The high water dentifrice to be tested is prepared as a suspension at the same concentration as the pyrophosphate and submitted to the same brushing regime. The precipitated silica to be tested is prepared as a suspension of 6.25 g in 50 ml of 0.5% aqueous solution of sodium carboxymethyl cellulose and submitted to the same brushing regime.

The preferred silica thickener is also an amorphous precipitated silica such as Zeodent® 165 silica. Other preferred silica thickeners are Zeodent® 163 and Zeofree® 153 silicas also available from J. M. Huber Corporation. Typical properties of these silicas are listed in Table C below.

TABLE C

| | Oil Abs. cm³/100 g | APS μm | BET m²/g | Pore Vol. cm³/g | Pour density g/cm³ | Pack Density g/cm³ |
|---|---|---|---|---|---|---|
| Zeodent 165 | 219 | 15 | 179 | 5.9 | 0.11 | 0.18 |
| Zeodent 163 | 198 | 11 | 213 | 3.9 | 0.12 | 0.19 |
| Zeodent 153 | 178 | 13 | 82 | 3.6 | 0.15 | 0.23 |

Other conventionally known silica thickeners agents suitable for dentifrice applications also could be used, singly or in combinations thereof.

The binder, which also can be referred to herein as a "gum thickener", is preferably selected from the group consisting of natural gums such as xanthan gum, carrageenan, cellulose gum, gum tragacanth, and/or synthetic gums such as alkali metal carboxymethyl cellulose (e.g., sodium carboxymethyl cellulose), hydroxyethyl cellulose, polyvinyl pyrrolidone, starch, water-soluble carboxyvinyl polymer, and polyacrylic acids or water-soluble polyacrylic acid salts, as used singly or in combinations thereof. For example, a suitable binder is sodium carboxymethyl cellulose (SCMC). Suitable SCMC having about 0.6 to about 0.8 carboxymethyl groups per anhydroglucose units are available such as Aqualon's CMC-7MXF product. The binder or gum thickener is utilized to provide cohesion to the composition and is preferably added to the composition in an amount sufficient to obtain a viscosity of greater than 200,000 centipoise in the resultant dentifrice composition. More preferably, the binder or gum thickener is added in an amount to obtain a viscosity of between 220,000 to 500,000 centipoise after 6 weeks of aging at room temperature (about 23° C.). When the abrasive polishing material is liberated from the binders during toothbrushing activity, the binders are water-soluble in the mouth. The binder is used in an amount of about 0.5 to about 1.5% by weight, and more preferably about 1.0% by weight to about 1.5% by weight, of the dentifrice composition of this invention. Binder amounts smaller than about 0.5% by weight will not permit sufficient viscosity and paste stability to be imparted to the dentifrice composition to meet the viscosity criterion set forth herein, while binder amounts exceeding about 1.5% by weight have been found to result in dentifrice compositions that tend to be lumpy and/or too sticky.

Another advantageous component of the dentifrice composition of the present invention is a polyol humectant. The polyol humectant is added in an amount sufficient to facilitate and ensure moisture retention by the dentifrice composition so as to prevent drying out of the dentifrice composition upon its exposure(s) to air. The humectant also adds sweetness. In the preferred embodiment the polyol humectant is selected from the group consisting of glycerin (glycerol), sorbitol, polyalkylene glycols such as polyethylene glycol and polypropylene glycol, hydrogenated starch hydrolyzates, xylitol, lactitol, hydrogenated corn syrup, and other edible polyhydric alcohols, used singly or as mixtures thereof. The polyalkylene glycols useful as the humectant generally have an average molecular weight ranging between about 200 and 3,700. The polyalkylene glycol should be used in an amount and with a molecular weight consistent with the overall viscosity requirements of the inventive dentifrice formulation. The polyol humectant can be used alone or in combination with other types of humectants suitable for dentifrice compositions.

Other adjuvants, additives, and materials can be added to the dentifrice composition of the present invention such as flavoring agents, foaming agents (e.g., sodium lauryl sulfate), detergents or surfactants, coloring or whitening agents (e.g., titanium dioxide, FD&C dyes,), preservatives (e.g., sodium benzoate, methyl paraben), and other materials typically found in dentifrice compositions. The optional additional adjuvants typically are present in small amounts, if present, at no greater than about 5% by weight each.

The ingredients of the dentifrice formulation typically and preferably are completely and uniformly blended. The dentifrice formulation can be conveniently dispensed in ribbon-like form with good body and texture, for example, from a collapsible squeeze tube or a manual pump dispenser. The liquid dentifrice formulation of this invention does not overly sag into bristles of a toothbrush due to its high viscosity, yet the texture of the dentifrice formulation is not lumpy or overly tacky either.

Exemplary, non-limiting methods of preparing high water content dentifrice compositions of the present invention are illustrated in the following examples.

Example 1

In this and the following examples, the following protocol was used to formulate the dentifrice compositions, unless specifically indicated otherwise in the respective examples. A "premix" was made by adding carboxymethyl cellulose (CMC) to batch water in a Heidolph RZR 2051 mixer available from Heidolph Elektro Gmbh & Co. KG, Germany. The CMC and water mixture were mixed under high shear for approximately 30 minutes at room temperature. The resulting mixture was lump free. Thereafter, sorbitol (70% solids by weight) and melted polyethylene glycol (PEG) were added to the mixer and the resultant mixture was mixed for about 5 minutes. PEG was warmed above room temperature (melted) to ease dispersion. Thereafter, fluoride, saccharin, sodium benzoate and titanium dioxide were added and the resultant mixture was mixed for about 15 minutes. The resultant mixture constituted the "premix."

The premix was then transferred into a vacuum mixer (Stephan UMC-5 available from A.Stephan u. Sohne Gmbh & Co., Germany). Silica abrasive (Zeodent® 113) and silica thickener (Zeodent® 165) were added to the premix and mixed for 20 minutes under vacuum at 400 rpm. Flavoring and sodium lauryl sulfate were added and the combination was mixed under vacuum for about 5 to 7 minutes at 400 rpm. The resulting toothpaste was removed from the mixer and placed in 50 cc plastic toothpaste tubes, sealed and stored for testing.

Toothpaste viscosity was measured with a Brookfield Viscometer Model No. DV II outfitted with a Helipath Stand and Helipath T-E spindle. The bottom of a toothpaste tube was cut off exposing the toothpaste sample. The tube was held with the open end upwards by placing the tube in a small beaker or other suitable container. The viscometer was set to 5 rpm and viscosity readings were recorded every 10 seconds for 1 minute for a total of 6 readings. The 6 readings were averaged and reported as the viscosity at the current age of the paste. Viscosity is typically determined after one, three and six weeks aging at room temperature. It may also be tested after accelerated aging at 50° C. for extended periods. For accelerated aging, the toothpaste samples are brought to room temperature (about 23° C.) before viscosity testing. Unless indicated otherwise, viscosity values mentioned in this application are to be determined by the above-indicated protocol after aging a dentifrice composition sample for six weeks at room temperature (about 23° C.).

Aesthetic properties of toothpaste (stand-up, gloss, separation) were measured visually. About a one inch ribbon of toothpaste was squeezed from a tube onto a piece of ordinary white notebook paper. After waiting 3–5 minutes, aesthetic properties observations were recorded.

Stand-up refers to the shape of the toothpaste ribbon and relates to the paste's ability to stay on top of a toothbrush without sinking in-between the bristles. "Good" stand-up means the ribbon retained its shape. "Poor" stand-up means the ribbons flattens out, losing its shape.

Gloss refers to the surface appearance of the toothpaste. Toothpaste that has lost its glossy appearance is drying out, sometimes indicating too little humectant in the formulation. A glossy toothpaste is preferred over one with a matte finish. Ratings are either "glossy" or "matte".

Separation refers to the toothpaste formulation's integrity. Solid and liquid phases of the toothpaste may separate, usually due to too little binder or thickener. Liquid will be visible around the squeezed ribbon of paste if there is separation. Separation ratings are "none" (no separation); "slight" (small amount of liquid around ribbon); and "major" (major phase separation).

Table 1 sets forth two affordable toothpaste formulations and their corresponding viscosity and aesthetic properties. These formulations were prepared according to the procedure described above using the quantities of ingredients listed in Table 1.

TABLE 1

|  | 1A | 1B |
| --- | --- | --- |
| Ingredients |  |  |
| Deionized Water | 51.00 | 54.00 |
| Sorbitol, 70.0% | 21.00 | 18.00 |
| Cekol 2000 SCMC[a] | 1.20 | 1.20 |
| Titanium Dioxide | 0.41 | 0.41 |
| Sodium Fluoride | 0.24 | 0.24 |
| Sodium Saccharin | 0.20 | 0.20 |
| Methyl paraben | 0.00 | 0.00 |
| Sodium Benzoate | 0.50 | 0.50 |
| Zeodent ® 113 silica | 16.00 | 16.00 |
| Zeodent ® 165 silica | 8.00 | 8.00 |
| Sodium Lauryl Sulfate | 0.80 | 0.80 |
| Flavor | 0.65 | 0.65 |
| Total grams | 100.00 | 100.00 |
| % Total water[b] | 57.3 | 59.4 |
| Toothpaste number |  |  |
| Viscosity, 23° C. |  |  |
| 1 week | 302,000 | 291,000 |
| 3 weeks | 381,000 | 346,330 |
| 6 weeks | 508,000 | 488,170 |
| Separation | Slight | Slight |
| Gloss | Glossy | Glossy |
| Standup | Good | Good |

[a]Cekol 2000 SCMC is a carboxymethyl cellulose available from Metsa Specialty Chemicals, Nijmegen, The Netherlands
[b]Total water was calculated as the sum of the deionized water added to the batch plus the amount of water contributed from the sorbitol solution.

As can be seen from the data in Table 1, Example 1A and 1B formulations had acceptable viscosity and aesthetic properties.

Example 2

Nine therapeutic opaque toothpaste batches were prepared according to the process described above in Example 1 using the quantities of ingredients listed in Table 2. These batches all contained more than 63% total water. The batches represent two different types of carboxymethyl cellulose (CMC) gums, three different silica abrasives and two different silica thickeners. All batches had acceptable aesthetic properties and viscosity after 6 weeks.

TABLE 2

| Affordable Toothpaste Formulations - 60% Water | | | | | | | | | |
| --- | --- | --- | --- | --- | --- | --- | --- | --- | --- |
|  | 2A | 2B | 2C | 2D | 2E | 2F | 2G | 2H | 2I |
| Ingredients | | | | | | | | | |
| Deionized Water | 60.00 | 60.00 | 60.00 | 60.00 | 60.00 | 60.00 | 60.00 | 60.00 | 60.00 |
| Sorbitol 70.0% | 14.46 | 14.56 | 12.46 | 14.46 | 14.46 | 12.46 | 12.36 | 12.46 | 10.36 |
| CMC-7MXF[c] | 1.10 | 1.00 | 1.10 | 0.00 | 0.00 | 0.00 | 1.20 | 1.10 | 1.20 |

TABLE 2-continued

Affordable Toothpaste Formulations - 60% Water

|  | 2A | 2B | 2C | 2D | 2E | 2F | 2G | 2H | 2I |
|---|---|---|---|---|---|---|---|---|---|
| CMC-9M3IXF[c] | 0.00 | 0.00 | 0.00 | 1.10 | 1.10 | 1.10 | 0.00 | 0.00 | 0.00 |
| Carbowax 600 PEG[d] | 2.00 | 2.00 | 2.00 | 2.00 | 2.00 | 2.00 | 2.00 | 2.00 | 2.00 |
| Titanium Dioxide | 0.30 | 0.30 | 0.30 | 0.30 | 0.30 | 0.30 | 0.30 | 0.30 | 0.30 |
| Sodium Fluoride | 0.24 | 0.24 | 0.24 | 0.24 | 0.24 | 0.24 | 0.24 | 0.24 | 0.24 |
| Sodium Saccharin | 0.10 | 0.10 | 0.10 | 0.10 | 0.10 | 0.10 | 0.10 | 0.10 | 0.10 |
| Sodium Benzoate | 0.50 | 0.50 | 0.50 | 0.50 | 0.50 | 0.50 | 0.50 | 0.50 | 0.50 |
| Abrasive silica |  |  |  |  |  |  |  |  |  |
| Zeodent ® 113 silica | 10.00 | 0.00 | 0.00 | 10.00 | 0.00 | 0.00 | 10.00 | 0.00 | 0.00 |
| Zeodent ® 115 silica | 0.00 | 10.00 | 0.00 | 0.00 | 10.00 | 0.00 | 0.00 | 10.00 | 0.00 |
| Zeodent ® 124 silica | 0.00 | 0.00 | 12.00 | 0.00 | 0.00 | 12.00 | 0.00 | 0.00 | 12.00 |
| Thickener silica |  |  |  |  |  |  |  |  |  |
| Zeodent ® 165 silica | 10.00 | 10.00 | 10.00 | 10.00 | 10.00 | 10.00 | 0.00 | 0.00 | 0.00 |
| Zeofree ® 153 silica | 0.00 | 0.00 | 0.00 | 0.00 | 0.00 | 0.00 | 12.00 | 12.00 | 12.00 |
| Sodium Lauryl Sulfate | 0.80 | 0.80 | 0.80 | 0.80 | 0.80 | 0.80 | 0.80 | 0.80 | 0.80 |
| Flavor | 0.50 | 0.50 | 0.50 | 0.50 | 0.50 | 0.50 | 0.50 | 0.50 | 0.50 |
| Total grams | 100.00 | 100.00 | 100.00 | 100.00 | 100.00 | 100.00 | 100.00 | 100.00 | 100.00 |
| % Total water | 64.34 | 64.37 | 63.74 | 64.34 | 64.34 | 63.74 | 63.71 | 63.74 | 63.11 |
| Toothpaste Example |  |  |  |  |  |  |  |  |  |
| Viscosity, 23° C. |  |  |  |  |  |  |  |  |  |
| 1 week | 244,670 | 177,830 | 285,670 | 154,000 | 172,830 | 213,500 | 207,670 | 171,500 | 243,670 |
| 3 weeks | 251,670 | 226,330 | 317,330 | 217,000 | 192,160 | 249,330 | 273,670 | 201,830 | 294,670 |
| 6 weeks | 346,000 | 311,000 | 374,000 | 220,500 | 214,000 | 283,000 | 285,670 | 231,330 | 314,000 |
| Separation | None | None | None | Slight | None | None | None | None | None |
| Gloss | Glossy | Glossy | Glossy | Glossy | Glossy | Glossy | Glossy | Glossy | Glossy |
| Standup | Good | Good | Good | Good | Good | Good | Good | Good | Good |
| Viscosity/Accelerated 50° C. |  |  |  |  |  |  |  |  |  |
| 3 weeks | 456,000 | 375,000 | 479,500 | 344,670 | 352,330 | 355,330 | 388,800 | 399,000 | 410,800 |
| 6 weeks | 567,000 | 513,670 | 654,400 | 491,000 | 438,000 | 476,330 | 423,330 | 402,670 | 590,670 |
| Separation | None | None | None | None | None | None | None | None | None |
| Gloss | Glossy | Glossy | Matte | Glossy | Glossy | Glossy | Glossy | Glossy | Glossy |
| Standup | Good | Good | Good | Good | Good | Good | Good | Good | Good |

Example 3

Four therapeutic opaque toothpaste batches were prepared according to the process described in Example 1 above using the ingredients and amounts thereof listed in Table 3 below. These batches contained more than 67% total batch water and still had acceptable aesthetic attributes and viscosity.

TABLE 3

Affordable Toothpaste Formulations - 65% Water

|  | 3A | 3B | 3C | 3D |
|---|---|---|---|---|
| Ingredients |  |  |  |  |
| Deionized Water | 65.00 | 65.00 | 65.00 | 65.00 |
| Sorbitol 70.0% | 9.36 | 9.46 | 9.36 | 7.36 |
| CMC-7MXF | 1.20 | 1.10 | 1.20 | 1.20 |
| CMC-9M31XF | 0.00 | 0.00 | 0.00 | 0.00 |
| Carbowax 600 PEG | 2.00 | 2.00 | 2.00 | 2.00 |
| Titanium Dioxide | 0.30 | 0.30 | 0.30 | 0.30 |
| Sodium Fluoride | 0.24 | 0.24 | 0.24 | 0.24 |
| Sodium Saccharin | 0.10 | 0.10 | 0.10 | 0.10 |
| Sodium Benzoate | 0.50 | 0.50 | 0.50 | 0.50 |
| Abrasive silica |  |  |  |  |
| Zeodent ® 113 silica | 10.00 | 0.00 | 0.00 | 10.00 |
| Zeodent ® 115 silica | 0.00 | 10.00 | 0.00 | 0.00 |
| Zeodent ® 124 silica | 0.00 | 0.00 | 10.00 | 0.00 |
| Thickener silica |  |  |  |  |
| Zeodent ® 165 silica | 10.00 | 10.00 | 10.00 | 0.00 |
| Zeofree ® 153 silica | 0.00 | 0.00 | 0.00 | 12.00 |
| Sodium Lauryl Sulfate | 0.80 | 0.80 | 0.80 | 0.80 |
| Flavor | 0.50 | 0.50 | 0.50 | 0.50 |
| Total grains | 100.00 | 100.00 | 100.00 | 100.00 |
| % Total Water | 67.81 | 67.84 | 67.81 | 67.21 |
| Toothpaste Example |  |  |  |  |
| Viscosity, 23° C. |  |  |  |  |
| 1 week | 232,000 | 175,000 | 229,000 | 193,170 |
| 3 weeks | 264,000 | 218,000 | 274,330 | 199,330 |
| 6 weeks | 346,330 | 238,670 | 304,000 | 249,600 |
| Separation | None | None | None | None |
| Gloss | Glossy | Glossy | Glossy | Glossy |
| Standup | Good | Good | Good | Good |
| Viscosity/Accelerated 50° C. |  |  |  |  |
| 3 Weeks | 485,330 | 437,000 | 375,000 | 314,330 |
| 6 Weeks | 525,670 | 442,800 | 475,330 | 400,670 |
| Separation | None | None | None | None |
| Gloss | Glossy | Glossy | Glossy | Glossy |
| Standup | Good | Good | Good | Good |

Example 4

Two high water toothpaste formulations were prepared as described above in Example 1 using the ingredients and amounts thereof listed in Table 4 below. RDA was measured on these toothpaste formulation. Both pastes had good aesthetic attributes in addition to acceptable abrasion levels.

TABLE 4

Affordable Toothpaste RDA Values

|  | Example 4A | Example 4B |
|---|---|---|
| Ingredients |  |  |
| Water | 65.0 | 50.21 |
| Zeodent ® 113 Silica abrasive | 12.0 | 16.0 |
| Zeodent ® 163 Silica Thickener | 13.0 | 9.0 |
| Sorbitol, 70% | 5.0 | 20.8 |
| Carbowax 600 PEG | 1.36 | 0.0 |
| Cekol 2000 SCMC | 1.2 | 1.2 |
| Sodium Lauryl Sulfate | 0.8 | 0.8 |
| Flavor | 0.5 | 1.0 |
| Sodium Benzoate | 0.5 | 0.0 |
| Methyl Paraben | 0.0 | 0.05 |
| Titanium Dioxide | 0.3 | 0.5 |
| Sodium Fluoride | 0.24 | 0.24 |
| Sodium Saccharin | 0.1 | 0.2 |
| Total grams | 100 | 100 |
| % Total Water | 66.5 | 56.45 |
| Toothpaste Properties |  |  |
| RDA | 65 | 85 |
| Viscosity, cP | 240,000 | 573,000 |
| Density | 1.185 | 1.231 |
| pH, 5% | 6.6 | 7.0 |

Example 5

Three high water affordable toothpaste batches were prepared as described above in Example 1 using the ingredients and amounts listed in Table 5 below. All formulations had good aesthetic properties and good sodium fluoride availability.

TABLE 5

|  | Example 5A | Example 5B | Example 5C |
|---|---|---|---|
| Ingredients |  |  |  |
| Water | 60 | 65 | 70 |
| Zeodent ® 623 Silica abrasive | 13.0 | 13.0 | 13.0 |
| Zeodent ® 163 Silica Thickener | 12.0 | 12.0 | 12.0 |
| Sorbitol, 70% | 11.46 | 5.0 | 0.0 |
| Carbowax 600 PEG | 0.0 | 1.36 | 1.16 |
| Cekol 2000 SCMC | 1.1 | 1.2 | 1.4 |
| Sodium Lauryl Sulfate | 0.8 | 0.8 | 0.8 |
| Flavor | 0.5 | 0.5 | 0.5 |
| Sodium Benzoate | 0.5 | 0.5 | 0.5 |
| Titanium Dioxide | 0.3 | 0.3 | 0.3 |
| Sodium Fluoride | 0.24 | 0.24 | 0.24 |
| Sodium Saccharin | 0.1 | 0.1 | 0.1 |
| Total grams | 100 | 100 | 100 |
| % Total Water | 63.44 | 66.5 | 70 |
| Toothpaste Properties |  |  |  |
| Fluoride Availability, 6 weeks | 87.5 | 92.5 | 91.7 |
| Viscosity, cP, 1 week | 540,000 | 586,000 | 542,000 |
| Density | 1.194 | 1.181 | 1.164 |
| pH, 5% | 6.9 | 6.9 | 6.9 |

Fluoride availability in toothpaste was determined with a fluoride specific ion electrode (Orion #94-09A) connected to an Orion EA940 meter. Specifically, 10 g toothpaste was slurried in 30 mL deionized water then centrifuged at 11,000 rpm for about 15 minutes. 10 ml of the resulting clear supernatant and 10 ml buffer were placed into a beaker and the concentration of fluoride was read directly from the meter which was previously calibrated using 100 ppm and 1000 ppm F standards. The buffer consisted of 0.2N EDTA/ 0.2N THAM (2-amino-2-(hydroxymethyl)-1,3-propanediol) adjusted to pH 8.0 with 5N NaOH.

The present invention may be embodied in other specific forms without departing from the spirit or essential attributes thereof and accordingly reference should be made to the appended claims rather than the foregoing specification as indicating the scope of the invention.

What is claimed is:

1. A high water content dentifrice composition comprising:

water in an amount ranging from about 60% to about 70% by weight;

abrasive material in an amount of about 8% to about 18% by weight, wherein said abrasive material is an amorphous silica;

silica thickener in an amount of about 8% to about 15% by weight;

gum thickener in an amount of about 0.5% to about 1.5% by weight;

polyol humectant in an amount of about 1% to about 20% by weight; and wherein the dentifrice composition has a viscosity of greater than about 200,000 cP.

2. The composition of claim 1, wherein said amorphous silica abrasive has a RDA value of about 30 to about 150.

3. The composition of claim 1, having a viscosity from about 220,000 to about 500,000 cP.

4. The composition of claim 1, having a viscosity from about 200,000 to about 500,000 cP.

5. The composition of claim 1, wherein said polyol humectant comprises sorbitol.

6. The composition of claim 1, further comprising an anti-caries agent in an effective amount.

7. The composition of claim 1, further comprising an water-soluble source fluoride selected from the group of sodium fluoride, sodium monofluorophosphate, stannous fluoride, potassium fluoride, potassium stannous fluoride, chlorhexidine, sodium fluorostannate, stannous chlorofluoride, and amine fluoride.

8. The composition of claim 1, wherein the composition comprises a substantially uniform and substantially complete mixture of the water, abrasive material, silica thickener, gum thickener, and polyol humectant.

9. The composition of claim 1, wherein said amorphous silica comprises amorphous precipitated silica.

10. The composition of claim 1, wherein said silica thickener comprises amorphous precipitated silica.

11. The composition of claim 1, wherein said amorphous silica comprises amorphous precipitated silica, and said silica thickener comprises amorphous precipitated silica.

12. The composition of claim 1, wherein said gum thickener comprises alkali metal carboxy methylcellulose, and the polyol humectant comprises sorbitol.

13. A high water content dentifrice composition comprising:

water in an amount ranging from about 60% to about 85% by weight;

abrasive amorphous precipitated silica material in an amount of about 8% to about 18% by weight;

amorphous precipitated silica thickener in an amount of about 8% to about 15% by weight;

alkali metal carboxy methylcellulose in an amount of about 0.5% to about 1.5% by weight;

sorbitol in an amount of about 1% to about 20% by weight; and wherein the dentifrice composition has a viscosity of greater than about 200,000 cP.

* * * * *